United States Patent [19]

Huge-Jensen

[11] Patent Number: 5,614,189
[45] Date of Patent: Mar. 25, 1997

[54] RECOMBINANTLY PRODUCED LIPASES FOR THERAPEUTICAL TREATMENT

[75] Inventor: Birgitte Huge-Jensen, Jaegerspris, Denmark

[73] Assignee: Novo Nordisk A/S, Bagsvaerd, Denmark

[21] Appl. No.: 318,036

[22] Filed: Oct. 4, 1994

Related U.S. Application Data

[63] Continuation of Ser. No. 937,858, filed as PCT/DK91/00149 Jun. 4, 1991, abandoned.

[30] Foreign Application Priority Data

Jun. 6, 1990 [DK] Denmark .................................. 1379/90
Jul. 19, 1990 [DK] Denmark .................................. 1735/90

[51] Int. Cl.$^6$ ..................... A61K 38/46; A61K 38/54; C12N 15/55
[52] U.S. Cl. ..................... 424/94.6; 424/94.2; 435/198
[58] Field of Search ........................ 424/94.2, 94.6; 435/198

[56] References Cited

U.S. PATENT DOCUMENTS 4,659,667  4/1987  Brewer et al. ..................... 435/222

FOREIGN PATENT DOCUMENTS 0305216    3/1989   European Pat. Off. .
305216     3/1989   European Pat. Off. .
WO86/01532 3/1986   WIPO .

OTHER PUBLICATIONS

Huge–Jensen, B. et al.; Lipids 24:781–785 (1989).
Brady, L. et al.; Nature 343:767–770 (1990).
Roberts, I.M.; Pancreas 4:496–503 (1989).
Ollis, D. et al.; Meth. Enzymol. 182:646–659 (1990).

*Primary Examiner*—Robert A. Wax
*Assistant Examiner*—Eric Grimes
*Attorney, Agent, or Firm*—Steve T. Zelson, Esq.; Elias J. Lambiris, Esq.

[57] ABSTRACT

This invention relates to lipase containing pharmaceutical compositions comprising a microbial, 1, 3-position specific, crystalline lipase and to methods for treatment or prophylaxis of lipase deficiency in mammals.

14 Claims, 7 Drawing Sheets

RECOMBINANTLY PRODUCED LIPASES FOR THERAPEUTICAL TREATMENT

This application is a continuation application of application Ser. No. 07/937,858 filed Oct. 16, 1992, now abandoned which is a 35 U.S.C. 371 national application of PCT/DK91/00149 filed Jun. 4, 1991, which are incorporated herein by reference.

FIELD OF INVENTION

The present invention is directed towards the use of recombinantly produced microbial lipases in therapeutical applications. More specifically microbial lipases of high purity are provided for the manufacture of pharmaceutical compounds for treatment of lipase deficiency. Further pharmaceutical compositions comprising these lipases are provided.

BACKGROUND

During the last decade the recombinant technology has provided new high yield processes allowing a variety of products to be obtained in high purity in an industrial scale. Among such products are lipases. These lipases have found different technical applications, e.g. in ester hydrolysis processes, ester synthesis processes, ester interchange reactions or within the detergent industry. However, these recombinantly produced microbial lipases have never found therapeutical applications.

For pancreatic enzyme replacement therapy lipase containing pharmaceutical preparations are available. Most of these preparations are mixtures of the various enzymes, proteases, amylases and lipases, along with other components, as the manufacture of these preparations is based mainly on extraction of porcine pancreatic enzymes. Such substitution preparations are expensive, and the therapeutic effect varies considerably within the preparations. Especially the amount of lipase in most preparations is too low to ensure adequate enzymatic degradation of the triglycerides in order to achieve a normal lipid absorption from the gastrointestinal tract. Furthermore the US FDA, in a press release of May 16, 1990 (P90-31), and a Federal Register Notice of Proposed Rule Making of the same date (FR 20434–20438), propose to ban a number of these enzymes sold as digestive aids, as the administration claims that these ingredients had not been proven effective.

Other lipase containing pharmaceutical preparations are based on lipases produced by microbiological cultivation of lipase producing fungi followed by recovery of the lipases from the culture broth, vide e.g. DE publication No. 16 42 654 and GB publication No. 1 442 677. These processes are low yield processes, causing a troublesome and uneconomic isolation and purification of the desired lipase.

From international patent application WO 86/01532 a human gastric lipase protein is known. Moreover, a process for producing this protein using recombinant DNA technology is described. Gastric lipases are of course of animal origin. Problems inherently associated with the expression of genes of animal origin in microorganisms compromise the use of many such processes in industrial scale. In these cases troublesome and uneconomic isolation and purification processes are still required to obtain a sufficiently purified lipase.

Oral substitution of exocrine pancreatic enzymes is of key importance in the treatment of humans suffering from severe exocrine pancreatic insufficiency, such as cystic fibrosis and chronic pancreatitis, which lead to malabsorption and steatorrhoea (fatty stools). Treatment improves the frequency, nature and size of the stools, but steatorrhoea is rarely abolished. Although conventional enzyme preparations can largely abolish protein and carbohydrate maldigestion, they are only partially able to improve the digestion of fats. The major reason for this failure of theoretically adequate dosages of conventional pancreatic enzyme preparations to completely eliminate steatorrhoea has been found to be inactivation of the lipase by gastric acid and pepsin.

Therapeutic alternatives for supplementary therapy with conventional pancreatic enzyme preparations are acid stabilized or acid protected preparations. However, due to a generally decreased pH in the duodenum and small intestine in patients suffering from cystic fibrosis, enteric coated preparations may not release their content in an ordinary manner.

As an overall, treatment by conventional pancreatic enzyme preparations brings about serious disadvantages for the patients, as unpleasantly high amounts of granulate/capsules are required, causing nausea and reduction of appetite, yet not leading to total improvement.

It is an object of the present invention to obviate these shortcomings by providing recombinantly produced microbial lipases of high purity for the manufacture of pharmaceutical compositions, with increased lipase content.

BRIEF DISCLOSURE OF THE INVENTION

It has now been found that it is possible to increase lipase dosage in the order of magnitude of 5 to 40 times without being unpalatable and causing nausea. Moreover, it has surprisingly been found that a solution of a crystalline lipase is more stable than a solution of a non-crystalline lipase, thus causing reduced loss of activity during passage through the stomach.

Accordingly, in its first aspect, the present invention provides a crystalline lipase for use in the manufacture of pharmaceutical compositions for treatment of lipase deficiency. Preferred lipases are *Rhizomucor miehei* lipases and Humicola lipases, particularly *Humicola lanuginosa* lipase. Preferably these lipases are recombinantly produced lipases.

In a second aspect, the invention provides a recombinantly produced lipase for use in the manufacture of pharmaceutical compositions for treatment of lipase deficiency. Preferably these lipases are of high purity.

In a third aspect, the invention provides a lipase containing pharmaceutical composition comprising a lipase of high purity. Preferably this lipase is crystalline, and preferably the lipase is a Rhizomucor miehei lipase or a Humicola lipase, particularly a Humicola lanuginosa lipase.

In a fourth aspect, the invention provides a lipase containing pharmaceutical composition comprising a recombinantly produced lipase. Preferably this lipase is a *Rhizomucor miehei* lipase or a Humicola lipase, particularly a *Humicola lanuginosa* lipase. More preferably the lipase is of high purity.

BRIEF DESCRIPTION OF THE DRAWINGS

The present invention is further illustrated by reference to the accompanying drawings, in which:

FIG. 2: Soybean oil

FIG. 3: Cod liver oil

FIG. 4: Coconut oil

FIG. 5: Olive oil

The three enzymes referred to in the figures are:

A: Recombinantly produced *Humicola lanuginosa* lipase

B: Recombinantly produced *Rhizomucor miehei* lipase

C: Pancreatin (Pankreatin Rosco enterogranulat)

Figure 6:
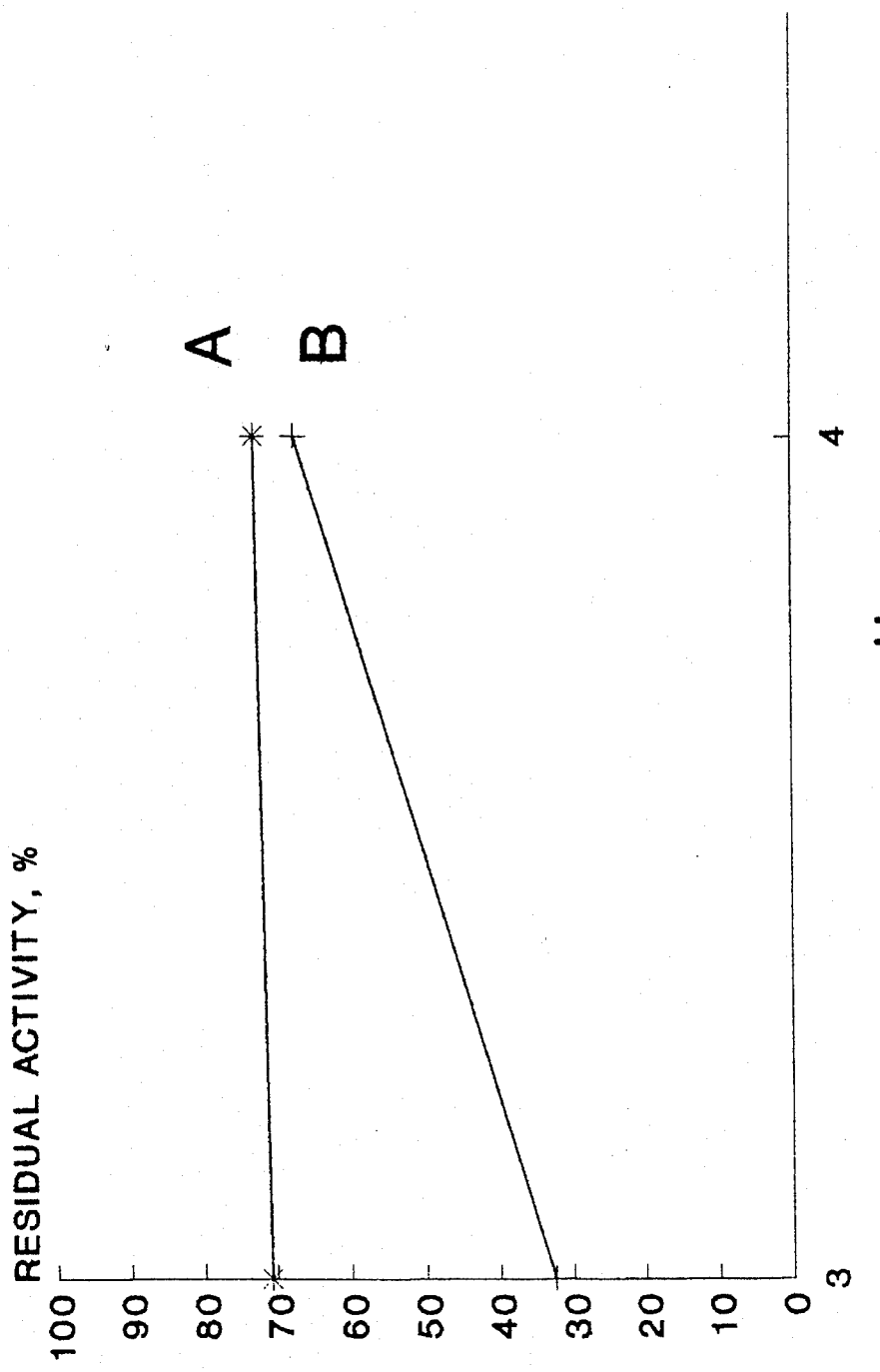
Figure 7:
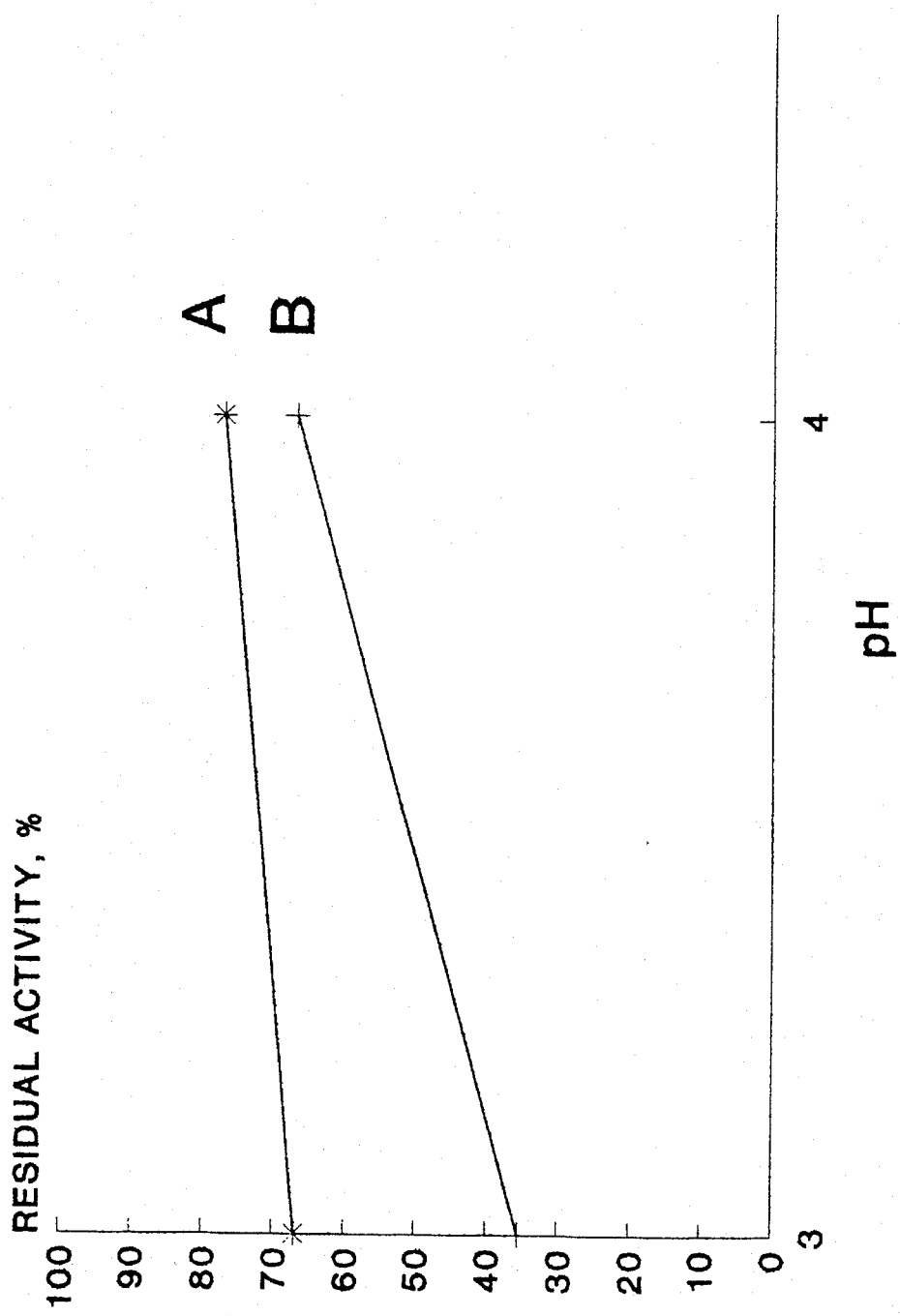

FIGS. 6–7 show the stabilizing effect of a crystalline lipase compared to the non-crystalline lipase at pH 3–4, determined by % residual activity (A: Crystalline *Humicola lanuginosa* lipase; B: Non-crystalline *Humicola lanuginosa* lipase)

FIG. 6: Lipase concentration 2500 LU/ml; Incubation 10 minutes.

FIG. 7: Lipase concentration 2000 LU/ml; Incubation 30 minutes.

DETAILED DISCLOSURE OF THE INVENTION

Therapeutical effects

In vitro experiments with recombinantly produced microbial lipase of the invention have now shown that although a reduction of activity takes place throughout the gastrointestinal tract, the activity of the recombinantly produced microbial lipase of the invention is at least as high as the activity of conventional pancreatin preparations, when compared on base of amount of dosed lipase. Consequently it is possible to obtain pharmaceutical compositions in amounts of doses which are not unpleasant to swallow.

The limiting factor for the therapeutical effect on lipid absorption in the gastrointestinal tract is the amount of active lipase available at the duodenum and upper part of the small intestine.

The enzyme activity remaining after passage through the stomach mainly depends on time of passage, acid stability of the enzyme and the stability of the enzyme towards proteolytic enzymes present in the gastric juice, such as pepsin. Using various forms of enteric coated preparations, the enzymes are more or less protected during passage through the gastric juice, but as previously mentioned, enteric coated preparations may not release their content in an ordinary manner, i.e. in the duodenum and upper part of the small intestine, due to a generally decreased pH in the duodenum and small intestine in patients suffering from cystic fibrosis. It is therefore of interest to know the fate of an enzyme released in the stomach.

Figure 1:
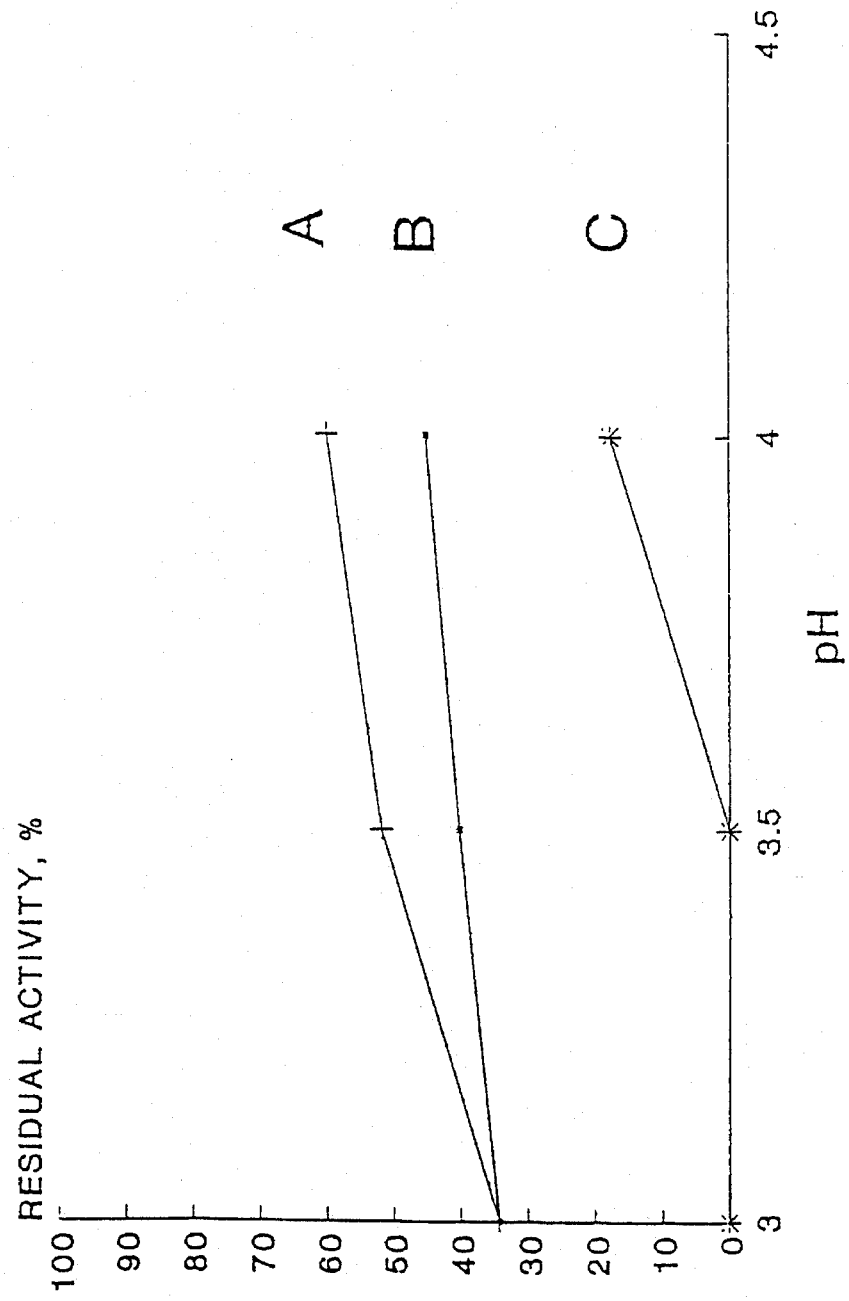
FIG. 1 shows a comparison of the stability against pepsin in the presence of substrate of three enzymes, A, B and C.
Figure 2:
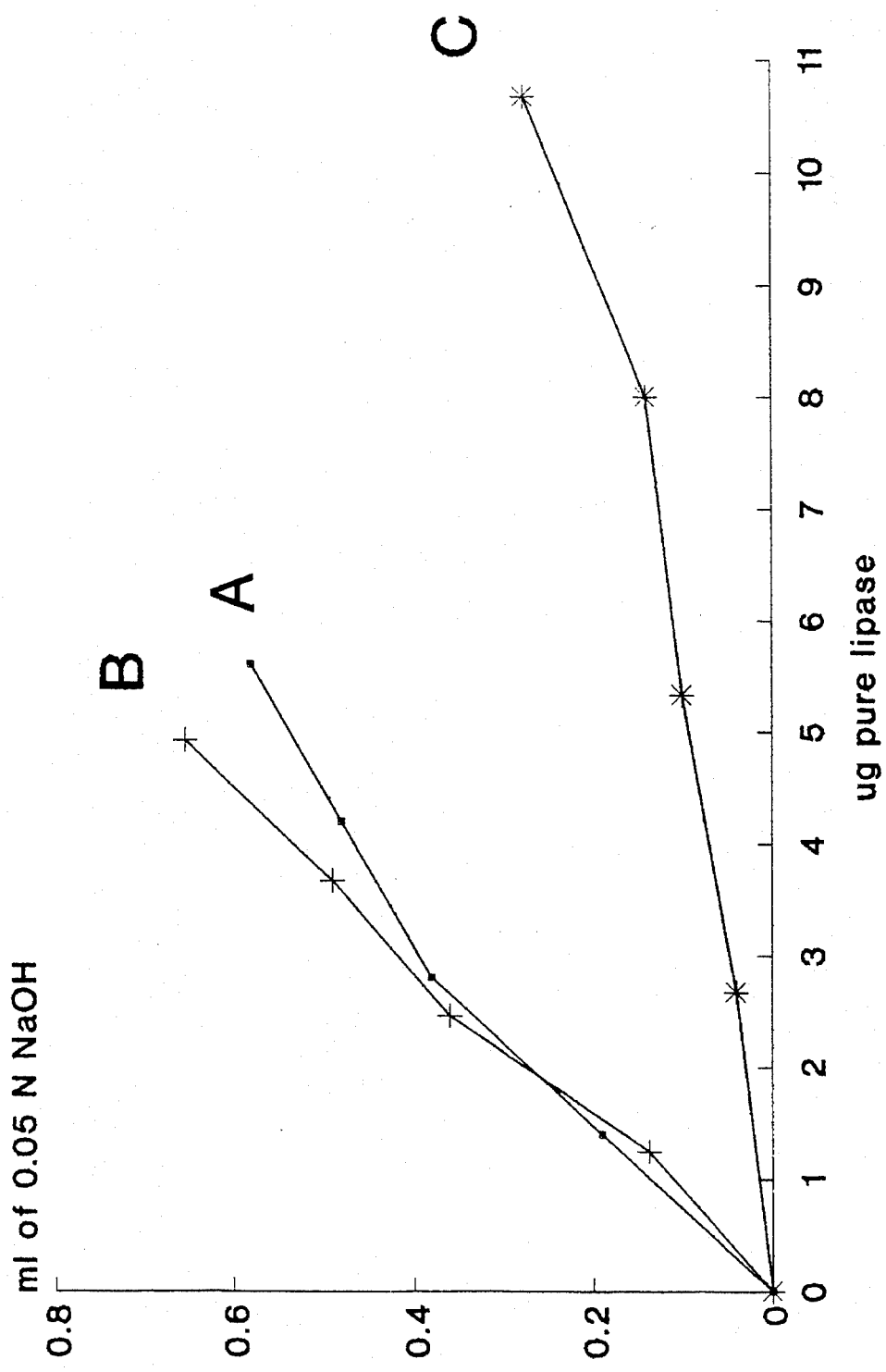
FIGS. 2–5 show a comparison of the activity on various substrates of three enzymes, A, B and C. The substrates are.
Figure 3:
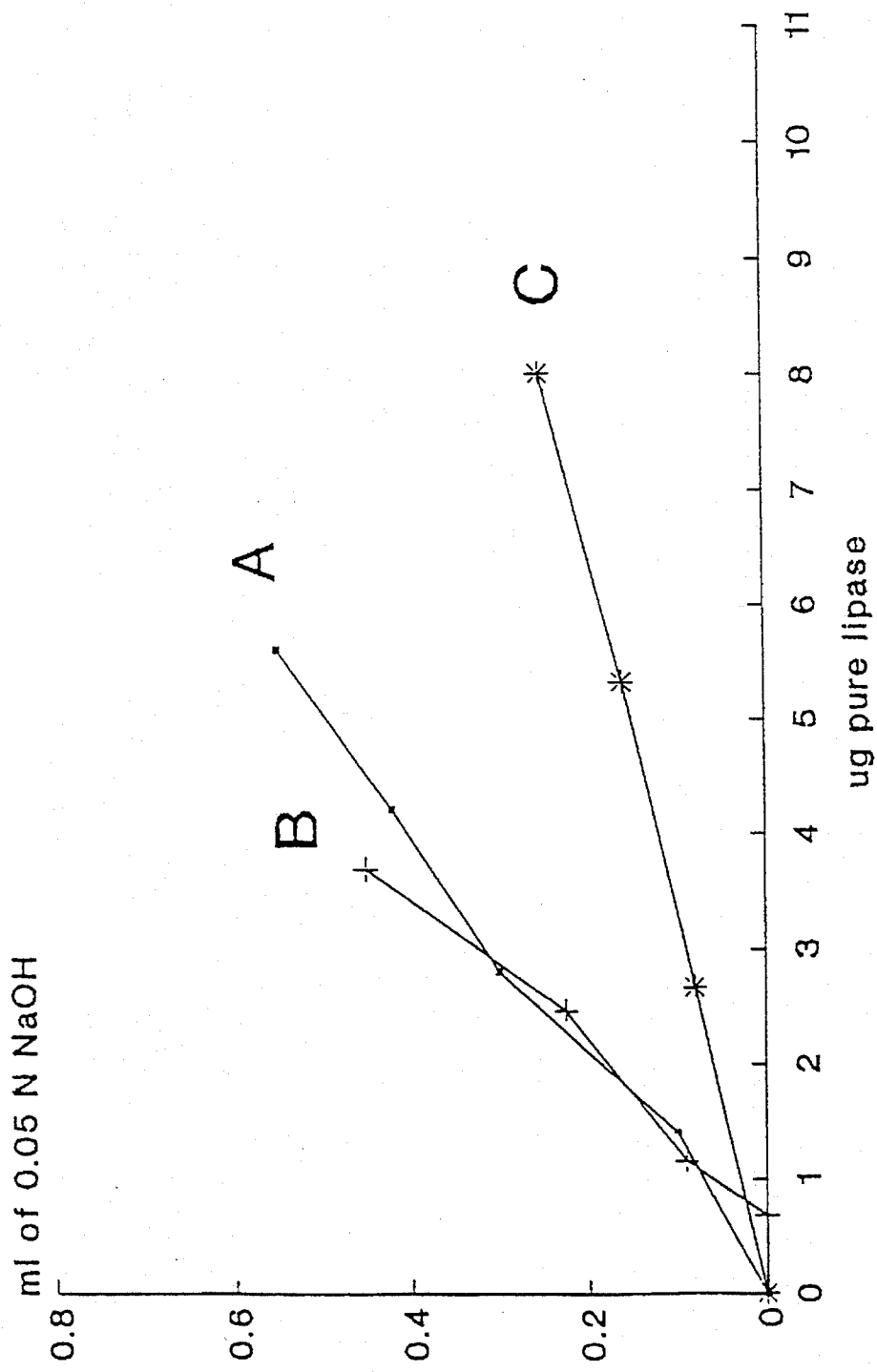
Figure 4:
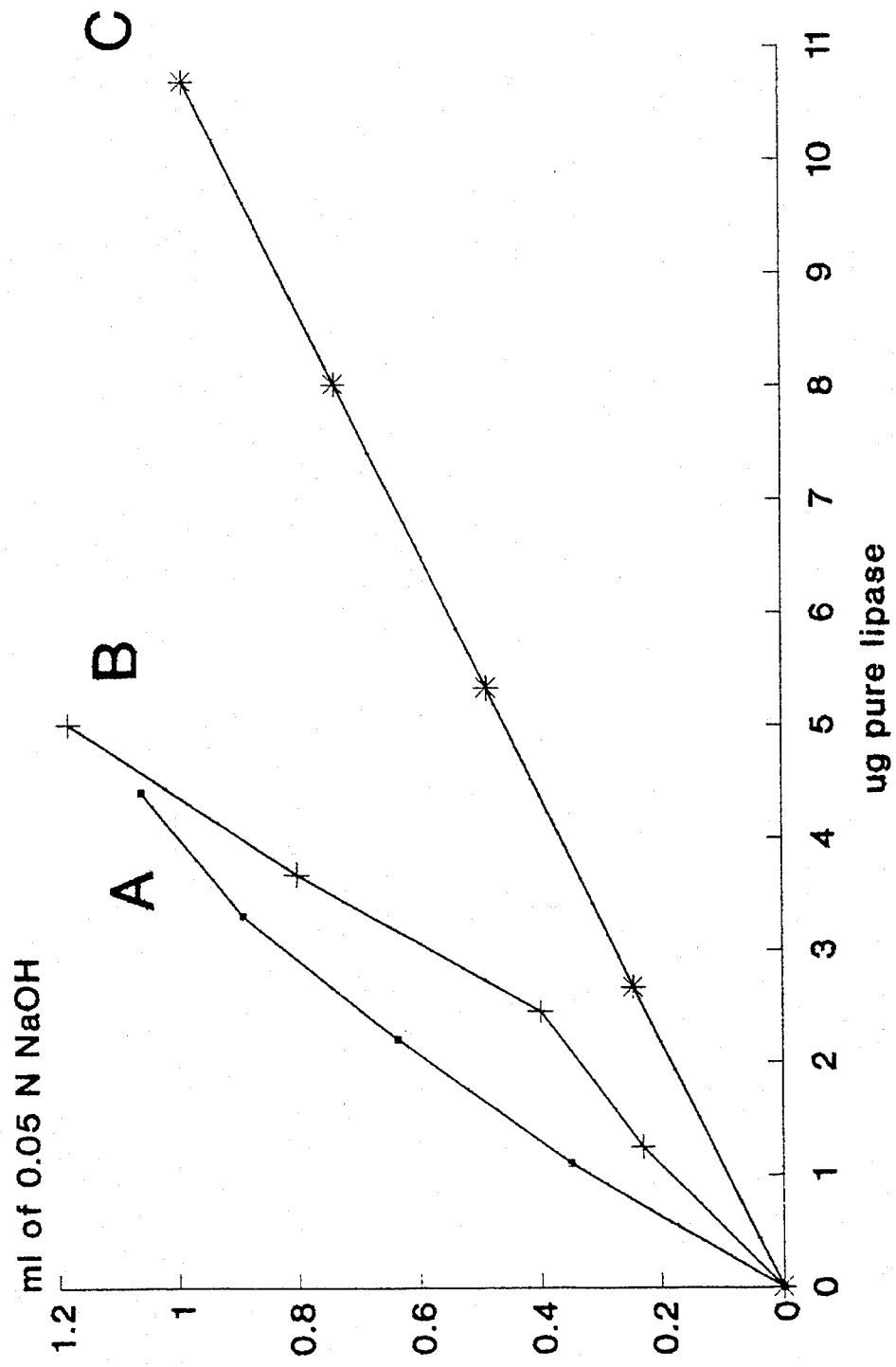
Figure 5:
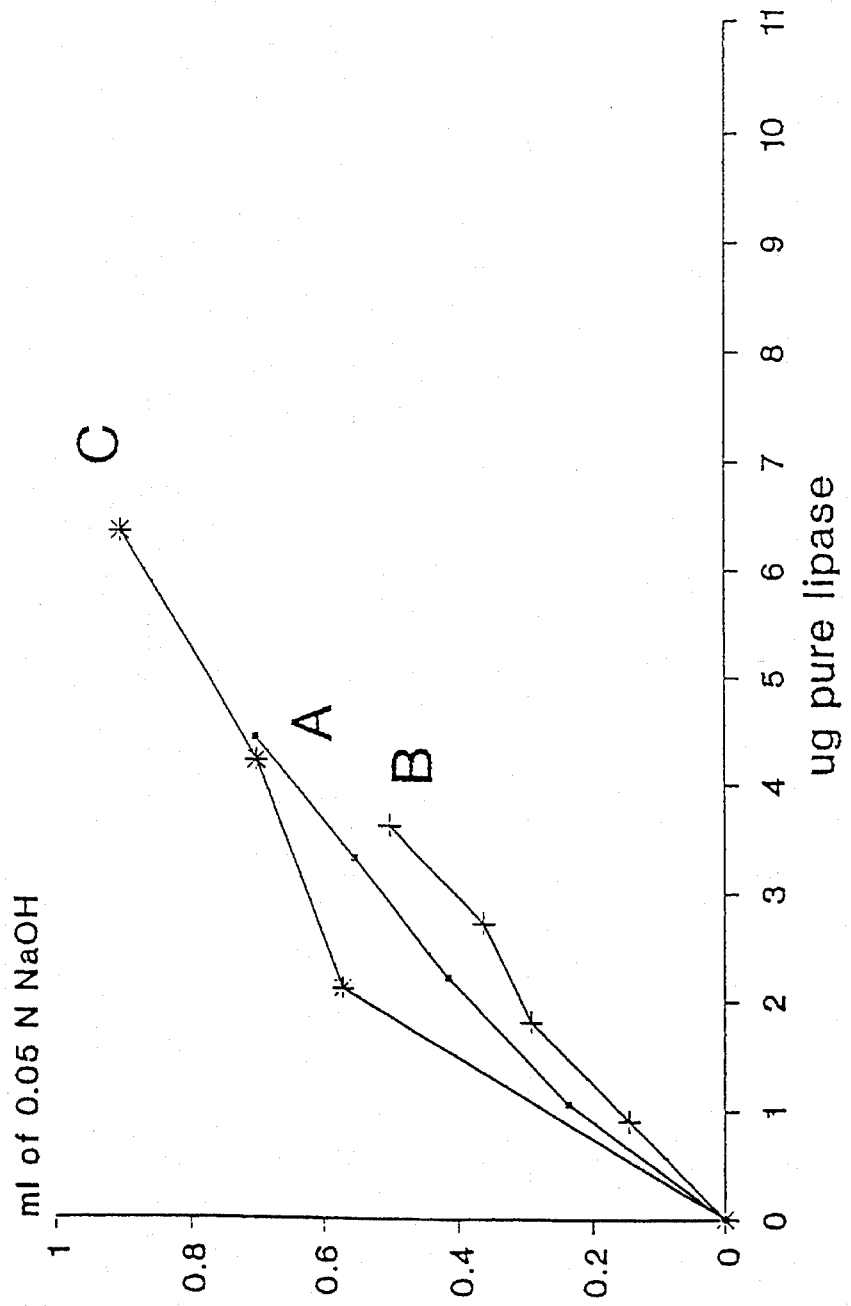

In FIG. 1 the result of an in vitro stability test, performed under gastric conditions, is shown. At the beginning of a meal the pH in the stomach may rise to around pH 5, and during digestion the pH decreases to around pH 2. For a stability test a pH in the range of 3 to 4 is considered relevant. The results indicate that a recombinantly produced microbial lipase of the invention will survive in the stomach when or if released here, contrary to conventionally produced pancreatin. Hence the lipase is able to exert its action at the moment it reaches the duodenum. Experimental data are cited in Example 2.

From in vitro experiments it has been found that a crystalline lipase shows a significantly reduced rate of dissolution at low pH and room temperature, compared to the non-crystalline lipase. Moreover, it has surprisingly been found that a solution of a crystalline lipase (i.e. the former crystalline lipase being fully dissolved) is more stable than a solution of the non-crystalline lipase at pH 3–4. This effect is demonstrated in Example 4. In the result the loss of activity during passage through the stomach can be considerably reduced when the lipase is crystalline.

In the duodenum and the intestine the lipase activity is greatly influenced by the bile salts present. In Example 3, Table 2, the results of an experiment showing the effect of bile salts are set up. Further, the experiment was performed as a comparison between the specific activity of two of the recombinantly produced microbial lipases of the invention and a conventionally produced pancreatin. As expected the conventionally produced pancreatin composition shows increased activity in the presence of bile salts, due to the action of co-factors originating from the extraction process.

Surprisingly, and as shown in FIGS. 2–5, the activity of the recombinantly produced microbial lipase of the invention is at least as high as the activity of the conventionally prepared pancreatin, when compared on base of amount of dosed lipase. The performance, based on amount of pure lipase, was investigated using the method described in Example 3, and the results are shown in FIGS. 2–5. From FIGS. 2–4 it is seen that both A and B are superior to C. From FIG. 5 it is seen that the three preparations performed equally well.

Recombinantly produced microbial lipases

By "recombinantly produced microbial lipase" is meant a lipase produced by way of recombinant DNA-technology, the lipase being of microbial origin.

In the context of this invention suitable lipases are recombinantly produced microbial lipases that posses lipolytic activity at relatively low pH.

The recombinantly produced microbial lipase may be a lipase variant or mutated lipase being functionally equivalent or having structural features similar to a naturally occurring lipase.

Preferred recombinantly produced microbial lipases are lipases derived from fungus, e.g. Humicola or Rhizomucor, or lipases derived from yeasts, e.g Candida, or lipases derived from bacteria, e.g. Pseudomonas. Most preferred are lipases derived from a strain of *Humicola lanuginosa* or *Rhizomucor miehei*.

The recombinantly produced microbial lipase may be obtained by fermentation of a fungal cell, e.g. belonging to the genus Asperqillus, such as *A. niger*, *A. oryzae*, or *A. nidulans*; a yeast cell, e.g. belonging to a strain of Saccharomyces, such as *S. cerevisiae*, or a methylotrophic yeast from the genera Hansenula, such as *H. polymorpha*, or Phichia, such as *P. pastoris*; or a bacterial cell, e.g. belonging to a strain of Bacillus, such as *B. subtilis*, or *B. lentus*; the cell being transformed with the gene encoding the microbial lipase. Most preferred host organisms are members of *Aspergillus oryzae*.

By a 1,3-position specific lipase is meant a lipase possessing preference for the hydrolysis of fatty acids in the outer positions of the triglycerides. Mammalian pancreatic lipase is a 1,3-position specific lipase, and so are the lipases derived from Rhizomucor sp. and Humicola sp.

Lipases of microbial origin of the invention and their production by recombinant technology are described in e.g. EP Publication Nos. 238,023 and 305,216, which publications are hereby included by reference.

A lipase variant or mutated lipase is obtainable by alteration of the DNA sequence of the parent gene or its derivatives. The lipase variant or mutated lipase may be expressed and produced when the DNA nucleotide sequence encoding the lipase is inserted into a suitable vector in a suitable host organism. The host organism does not necessarily have to be identical to the organism from which the parent gene originated. The methods for introducing mutations into genes are well known in the art, vide e.g. EP Patent Application No. 407,225.

Preferred lipase variants or mutated lipases are obtainable from parent microbial lipases. In a preferred embodiment the parent lipase is derived from a fungus, e.g. a strain of Humicola or Rhizomucor, preferably a strain of *Humicola lanuginosa* or a strain of *Rhizomucor miehei*. In another preferred embodiment the parent lipase is derived from a yeast, e.g. derived from a strain of Candida. In a further preferred embodiment the parent lipase is derived from a bacteria, e.g. derived from a strain of Pseudomonas. More preferred lipase variants or mutated lipases are lipase variants of parent lipases comprising a trypsinlike catalytic triad including an active serine residue located in a predominantly hydrophobic, elongated binding pocket of the lipase molecule, wherein the electrostatic charge and/or hydrophobicity of a lipid contact zone comprising residues located in the vicinity of the lipase structure containing the active serine residue, which residues may participate in the interaction with the substrate at or during hydrolysis, has been changed by deleting or substituting one or more negatively charged amino acid residues by neutral or positively charged amino acid residue(s), and/or by substituting one or more neutral amino acid residues by positively charged amino acid residue(s), and/or by deleting or substituting one or more hydrophobic amino acid residues by hydrophobic amino acid residue(s).

Isolation, purification and crystallization may be carried out by conventional means. In a preferred embodiment crystallization are carried out by adjustment of pH to a level around pI of the lipase and the presence of low concentrations of salts, i.e. 10 mS/cm or less.

Pharmaceutical compositions

A pharmaceutical composition of the invention includes any conventional pharmaceutical formulation that comprises a recombinantly produced microbial lipase of the invention, and that is suitable for oral administration, including powders, granulates and liquids; dose-formulated or not dose-formulated; monocomponent or multicomponent formulated; etc. A pharmaceutical composition of the invention may comprise the subsidiary materials known in the art.

The recombinantly produced microbial lipase of the invention can be administrated in doses ranging from 0.3 to 20 million LU per day, preferably 0.5 to 10 million LU per day, more preferred 1 to 10 million LU per day.

Preferred pharmaceutical compositions of the invention are dose-formulated, encapsulated monocomponent compositions and dose-formulated, encapsulated multicomponent compositions further comprising a protease and/or a carbohydrase.

With the use of a recombinantly produced microbial lipase of the invention for therapeutical treatment of lipase deficiency, an increase of lipase dosage in the order of magnitude of 5 to 40 times can be achieved. Thus it is now possible to obtain adequate daily lipase doses (1–10 million LU/day) by taking 2 to 20 capsules/day, in contrast to 90–900 capsules/day with a conventionally manufactured composition.

Other preferred pharmaceutical compositions of the invention are lipase containing liquid compositions for peroral administration. In such a composition the lipase may be formulated as a suspension of lipase crystals. Optionally these compositions also contain additives usually present in liquid peroral compositions, including flavoring agents and sweetening agents.

In a more specific aspect, a pharmaceutical composition of the invention is a lipase containing liquid composition for peroral administration comprising dietary nitrogen compounds and/or carbohydrates. Dietary nitrogen compounds may be a protein hydrolysate, preferably a vegetable protein hydrolysate such as a soy protein hydrolysate or a protein hydrolysate from faba bean, rape seed, oat, sesame and pea, or a mixture thereof. Preferably the protein hydrolysate should be non-bitter in the liquid pharmaceutical composition. In a preferred embodiment this pharmaceutical composition also contains additives usually present in peroral dietary products, including flavoring agents, sweetening.agents, minerals, trace elements, vitamins, and/or electrolytes. In this manner all nutritional and organoleptic demands can be met.

Lipase units

In this application the lipase activity is described by terms of Lipase Units (LU), defined as the amount of enzyme which liberates 1 µmol titratable butyric acid per minute under given standard conditions (i.e. tributyrine substrate, 30.0° C., and pH 7.0). A folder AF 95/5, describing this LU-assay, is available upon request from Novo Nordisk A/S, Denmark, which folder is hereby included by reference.

The following examples further illustrate the present invention.

EXAMPLE 1

Lipases of microbial origin were obtained by recombinant technology as described in EP Publication Nos. 238,023 and 305,216. An ultra filtration concentrate was diluted to 8% dry substance, and precipitated with 250 g $Na_2SO_4$/kg concentrate. The precipitate was filtered, and the filtercake was redissolved.

The lipase solution was ultra filtrated to a level of 20% dry substance, and salts were removed by diafiltration to obtain a concentrate with a conductance of approximately 5 mS/cm. The lipase solution was then subjected to filtration followed by a germfiltration. The resultant lipase solution contained approximately 18% dry substance.

The non-crystalline lipase was obtained by freeze drying of this lipase solution.

For preparation of the crystalline lipase pH of the lipase solution was adjusted to 4.3 with citric acid, and after 15 hours at 20° C. crystallization was accomplished. After filtration the crystals were freeze dried.

When compared on a SDS-PAGE the two preparations, the crystalline lipase and the non-crystalline lipase showed identical protein profiles.

EXAMPLE 2

An in vitro stability test was performed under gastric conditions, i.e. ½ hour at 37° C. at pH 3–4 and in the presence of substrate (olive oil) and pepsin. Two recombinantly produced microbial lipases (non-crystalline) of the invention were compared with a conventionally prepared pancreatin. The preparations were:

A: Recombinantly produced *Humicola lanuginosa* lipase
B: Recombinantly produced *Rhizomucor miehei* lipase
C: Pancreatin (Pankreatin Rosco enterogranulat)

The model substrate/incubation mixture contained:

| | |
|---|---|
| Olive oil | 3.3% |
| Lipase | 500–1200 LU/ml |
| Pepsin | 1 mg |

After incubation ½ hour at 37° C. the residual activity was determined by an LU-assay (tributyrin substrate, pH 7, 30° C., as described in a folder AF 95/5, available upon request from Novo Nordisk A/S, Denmark). The results are set up in FIG. 1.

EXAMPLE 3

In this in vitro activity test the influence of bile salts on the lipase activity is investigated. Further, the lipase activities of two recombinantly produced microbial lipases of the invention are compared to the activity of a conventionally prepared pancreatin preparation.

The experiment were performed at conditions as close as those happening in vivo (in the duodenum), such as at relevant pH 5.5, 37° C. and using a physiological concentration of bile salts, i.e. 8 mM. The bile salt composition is shown in Table 1.

TABLE 1

Bile salt composition

| COMPONENT | CONTENT ON MOLAR BASIS |
| --- | --- |
| Glycocholic acid | 29.8% |
| Glycochenodeoxycholic acid | 24.5.% |
| Glycodeoxycholic acid | 11.9% |
| Taurocholic acid | 12.6% |
| Taurochenodeoxycholic acid | 13.6% |
| Taurodeoxycholic acid | 7.6% |

In humans most of the triglycerides found in diets contain long chain fatty acids. Hence, lipase activities were investigated on various natural substrates in order to determine the activity as a function of chain length (number of carbon atoms in chain):

Olive oil (C18)

Refined soybean oil (C16,C18)

Coconut oil (C12, C14)

Cod liver oil (C16,C18,C20,C22)

Each triglyceride was emulsified with 10% gum arabic for 3 minutes and diluted to a 4% final concentration of oil with distilled water.

The enzymes were incubated at pH 5.5 with the substrate mixture for 4 minutes. Then full free fatty acid titration was achieved by a shift from the incubation pH to pH 9.0. Because of the high lipase activity at pH 9.0, a control was run in parallel (no incubation time) with the enzyme for each measurement, and its value was subtracted from the assay.

The lipase activities are expressed in terms of specific activities as lipase units (LU) per mg of enzyme powder, and the results are set up in Table 2.

TABLE 2

| SUB-STRATE | Specific activity on various substrates | | | | | |
| --- | --- | --- | --- | --- | --- | --- |
| | A | | B | | C | |
| | − | + | − | + | − | + |
| Olive oil | 2500 (100%) | 2450 (98%) | 2200 (100%) | 1540 (70%) | 11 (100%) | 24.5 (223%) |
| Soybean oil | 3090 (100%) | 920 (30%) | 2700 (100%) | 1380 (51%) | 2.6 (100%) | 10.5 (404%) |
| Coconut oil | 3060 (100%) | 2375 (78%) | 2780 (100%) | 2700 (97%) | 7.2 (100%) | 11.3 (157%) |
| Cod liver oil | 2375 (100%) | 630 (27%) | 1520 (100%) | 410 (27%) | 5.0 (100%) | 5.6 (112%) |

A: Recombinantly produced *Humicola lanuginosa* lipase
B: Recombinantly produced *Rhizomucor miehei* lipase
C: Pancreatin (Pankreatin Rosco enterogranulat)
−/+: measured in the absence/presence of bile salts
The specific activity is represented in units per mg preparation.

As expected the conventionally produced pancreatin composition shows increased activity in the presence of bile salts, due to the action of co-factors originating from the extraction process.

EXAMPLE 4

This example demonstrates the stabilizing effect of a crystalline lipase compared to a non-crystalline lipase. A *Humicola lanuginosa* lipase, obtained according to Example 1, is employed in this demonstration.

A model substrate/incubation mixture containing 3.3% olive oil was used. The lipase was dissolved in the substrate/reaction mixture within the first couple of minutes of the incubation. After incubation at 37° C. for 10 and 30 minutes, respectively, the residual activity was determined by an LU-assay (tributyrine substrate; pH 7; 30° C., as described in a folder AF 95/5, available upon request from Novo Nordisk A/S, Denmark).

In FIGS. 6–7 these experiments are presented (FIG. 6: Lipase concentration 2500 LU/ml, incubation 10 minutes; FIG. 7: Lipase concentration 2000 LU/ml, incubation 30 minutes). In these figures A designates the crystalline *Humicola lanuginosa* lipase, and B designates the non-crystalline *Humicola lanuginosa* lipase. It appears from the figures that after both 10 minutes and 30 minutes the crystalline lipase is more stable at pH 3–4, particularly at pH 3.

I claim:

1. A pharmaceutical composition comprising a therapeutically effective amount of a crystalline Humicola lipase and a pharmaceutically acceptable carrier, diluent, excipient and/or adjuvant.

2. The pharmaceutical composition according to claim 1, in which the lipase is a *Humicola lanuginosa* lipase.

3. The pharmaceutical composition according to claim 1, in which the lipase is obtained by fermentation of a strain of an Aspergillus species, transformed with a gene encoding the lipase.

4. The pharmaceutical composition according to claim 3, in which the transformed Aspergillus species is *Aspergillus oryzae*.

5. The pharmaceutical composition according to claim 1, which further comprises a protease and/or a carbohydrase.

6. The pharmaceutical composition according to claim 1, which is an encapsulated pharmaceutical composition.

7. The pharmaceutical composition according to claim 1, which is a liquid pharmaceutical composition for peroral administration.

8. The pharmaceutical composition according to claim 7, which further comprises flavoring agents and/or sweetening agents.

9. The pharmaceutical composition according to claim 7, which further comprises dietary nitrogen compounds and/or carbohydrates.

10. The pharmaceutical composition according to claim 7, which further comprises flavoring agents, sweetening agents, minerals, trace elements, vitamins, and/or electrolytes.

11. A method for treatment of lipase deficiency in a mammal, comprising administering to the mammal a therapeutically effective amount of a crystalline Humicola lipase.

12. The method according to claim 11, in which the lipase is a *Humicola lanuginosa* lipase.

13. The method according to claim 11, in which the crystalline lipase is obtained by fermentation of a strain of an Aspergillus species, transformed with a gene encoding the lipase.

14. The method according to claim 13, in which the transformed Aspergillus species is *Aspergillus oryzae*.

* * * * *